US006977252B1

(12) United States Patent
Kaneko et al.

(10) Patent No.: US 6,977,252 B1
(45) Date of Patent: Dec. 20, 2005

(54) USE OF 1,4-BENZOTHIAZEPINE DERIVATIVES AS DRUGS FOR OVERCOMING RESISTANCE TO ANTICANCER DRUGS

(75) Inventors: Noboru Kaneko, Tokyo (JP); Kazuhito Nishio, Chiba (JP); Takashi Nakamura, Nagasaki (JP)

(73) Assignee: Noboru Kaneko, (JP)

( * ) Notice: Subject to any disclaimer, the term of this patent is extended or adjusted under 35 U.S.C. 154(b) by 0 days.

(21) Appl. No.: 09/979,231

(22) PCT Filed: May 19, 2000

(86) PCT No.: PCT/JP00/03216

§ 371 (c)(1),
(2), (4) Date: Dec. 26, 2001

(87) PCT Pub. No.: WO00/71132

PCT Pub. Date: Nov. 30, 2000

(30) Foreign Application Priority Data

May 19, 1999 (JP) .................................. 11/139196

(51) Int. Cl.[7] ..................... A61K 31/55; A61K 31/445; A61K 31/435
(52) U.S. Cl. ........................... 514/211.07; 514/211.06; 514/211.05; 514/211.04; 514/211.03; 514/317; 514/315; 514/277
(58) Field of Search ..................... 514/211.07, 211.06, 514/211.05, 211.04, 211.03, 317, 315, 277

(56) References Cited

U.S. PATENT DOCUMENTS

| 5,416,066 A | 5/1995 | Kaneko et al. | 514/211 |
|---|---|---|---|
| 5,643,909 A | 7/1997 | Pfister et al. | 514/253 |
| 5,654,304 A | 8/1997 | Pfister et al. | 514/253 |
| 5,700,826 A | 12/1997 | Mjalli et al. | 514/397 |

FOREIGN PATENT DOCUMENTS

| JP | 57009712 | * 1/1982 |
|---|---|---|
| JP | 5-271208 | 10/1993 |
| JP | 2000-63287 | 2/2000 |
| WO | 92/12148 | 7/1992 |

OTHER PUBLICATIONS

Yan et al. "Increased sensitivity to anti-leukemia drugs by application of cyclosporin A and diltiazem", Shanghai Yixue (1998), 21(1), 10-13.*
Timcheva et al. Dokladi na Bulgarskata Akademiya na Naukite (1997), 50(5), 137-140.*
Hardman et al. "Goodman & Gilman's The Pharmacological Basis of Therapeutics" (9th ed, 1996) p. 51 and 57-58.*
Trisha Gura, Science, vol. 278, Nov., 1997, p. 1041-1042.*
Bull, "An Introduction to Physical Biochemistry" 1964, F.A. Davis Co. p. 103.*

M. Baba et al., "Relationship Between Multidrug Resistant Gene Expression and Multidrug Resistant-Reversing Effect of MS-209 in Various Tumor Cells," Cancer Chemother. Pharmacol. 36:361-367 (1995).
A. Bakka et al., "Resistance Against cis-Dichlorodiammineplatinum in Cultured Cells with a High Content of Mellothionein," Toxicol. Appl. Pharmacol. 61:215-226 (1981).
Y. Chuman et al., "Characterization of the ATP-Dependent $LTC_4$ Transporter in Cisplatin-Resistant Human KB Cells," Biochem. Biophys. Res. Comm. 226:158-165 (1996).

(Continued)

Primary Examiner—Shaojia Anna Jiang
(74) Attorney, Agent, or Firm—Ostrolenk, Faber, Gerb & Soffen, LLP

(57) ABSTRACT

The present invention relates to use of compounds represented by the following general formula [1] or salts or prodrugs thereof:

[I]

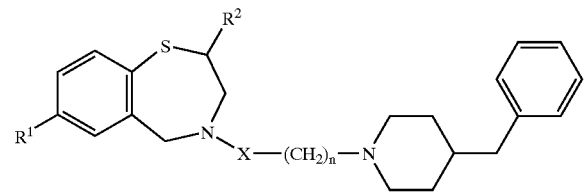

[where $R^1$ represents hydrogen atom or lower alkoxy group; $R^2$ represents hydrogen atom, lower alkoxy group, optionally substituted phenyl group,

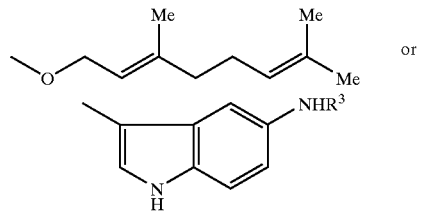

(where $R^3$ represents acyl group); X represents —CO— or —$CH_2$—; and n-represents 1 or 2], as drugs for overcoming a resistance to anticancer drugs or drugs for enhancing an effect of anticancer drugs. The compounds represented by the general formula [1] have not only a function of overcoming the resistance to various anticancer drugs but also a function of enhancing the effect of various anticancer drugs to anticancer-drug sensitive cells. Thus, these compounds have excellent effects on resistant cells and also on sensitive cells, and in particular effective in the treatment of a cancer having an acquired resistance to an anticancer drug.

6 Claims, No Drawings

OTHER PUBLICATIONS

S.P.C Cole et al., "Overexpression of a Transporter Gene in a Multidrug-Resistant Human Lung Cancer Cell Line," Science 258:1650-1654 (1992).

R-I Fujii et al., "Active Efflux System for Cisplatin in Cisplatin-Resistant Human KB Cells," Jpn. J. Cancer Res. 85:426-433 (1994).

Y. Fujiwara et al., "Determinants of Drug Response in a Cisplatin-Resistant Human Lung Cancer Cell Line," Jpn. J. Cancer Res. 81:527-535 (1990).

D.P. Gately et al., "Cellular Accumulation of the Anticancer Agent Cisplatin: A Review," Br. J. Cancer 67:1171-1176 (1993).

K. Hamaguchi et al., "Cross-Resistance to Diverse Drugs is Associated with Primary Cisplatin Resistance in Ovarian Cancer Cell Lines," Cancer Res. 53:5225-5232 (1993).

N. Kaneko, "New 1,4-Benzothiazepine Derivative, K201, Demonstrates Cardioprotective Effects Against Sudden Cardiac Cell Death and Intracellular Calcium Blocking Action," Drug. Dev. Res. 33:429-438 (1994).

S. Kondo et al., "Combination Therapy with Cisplatin and Nifedipine Inducing Apoptosis in Multidrug-Resistant Human Glioblastoma Cells," J. Neurosurg. 82:469-474 (1995).

Y. Kondo et al., "Metallothionein Null Cells have Increased Sensitivity to Anticancer Drugs," Cancer Res. 55:2021-2023 (1995.

K. Nakagawa et al., "Levels of Glutathione S Transferase π mRNA in Human Lung Cancer Cell Lines Correlate with the Resistance to Cisplatin and Carboplatin," Jpn. J. Cancer Res. 79:301-304 (1988).

K. Nakagawa et al., "Glutathione-S-Transferase π as a Determinant of Drug Resistance in Transfectant Cell Lines," J. Biol. Chem. 265:4296-4301 (1990).

J.M. Onoda et al., "In vivo Characterization of Combination Antitumor Chemotherapy with Calcium Channel Blockers and cis-Diamminedichloroplatinum (II)," Cancer Res. 49:2844-2850 (1989).

E. Reed et al., "Platinum-DNA Adduct in Leukocyte DNA of a Cohort of 49 Patients with 24 Different Types of Malignancies," Cancer Res. 53:3694-3699 (1993).

W. Sato et al., "Reversal of Multidrug Resistance by a Novel Quinoline Derivative, MS-209," Cancer Chemother. Pharmacol. 35:271-277 (1995).

K.J. Scanlon et al., "Cisplatin Resistance in Human Cancers," Pharmacol. Ther. 52:385-406 (1991).

T. Tsuruo et al., "Overcoming of Vincristine Resistance in P388 Leukemia in vivo and in vitro Through Enhanced Cytotoxicity of Vincristine and Vinblastine by Verapamil," Cancer Res. 41:1967-1972 (1981).

C.R. Wolf et al., "The Role of Glutathione in Determining the Response of Normal and Tumour Cells to Anticancer Drugs," Biochem. Soc. Transact. 15:728-730 (1987).

K. Yusa et al., "Reversal Mechanism of Multidrug Resistance by Verapamil: Direct Binding of Verapamil to P-Glycoprotein on Specific Sites and Transport of Verapamil Outward Across the Plasma Membrane of K562/ADM Cells," Cancer Res. 49:5002-5006 (1989).

M. Morita et al., "Ca channel blocking activity of JTV-519, a novel protective drug to cytotoxicity," Neuroscience Research Supplement No. 22, 1998, p. S65 XP001154969, 21st Annual Meeting of the Japan Neuroscience Society and the First Joint Meeting of the Japan Neuroscience Society and the Japanese Society for Neurochemistry, Tokyo, Japan, Sep. 21-23, 1998.

T. Nakamura et al., "Reversal of Cisplatin Resistance by the 1,4-Benzothiazepine Derivative, JTV-519," Jpn. J. Cancer Res. 92;597-602, Jun. 2001.

J.M. Onoda et al., "In Vivo Characterization of Combination of Antitumor Chemotherapy with Calcium Channel Blockers and cis-Diamminechloroplatinum (II)," Cancer Research 49(11):2844-2850, 1989.

T. Tsuruo et al., "Potentiation of antitumor agents by calcium channel blockers with special reference to cross-resistance patterns," Cancer Chemother. Pharmacol. 15:16-19, 1985.

Noboru Kaneko, "New 1,4-Benzothiazepine Derivative, K201, Demonstrates Cardioprotective Effects Against Sudden Cardiac Cell Death and Intracellular Calcium Blocking Action," Drug Development Research 33:429-438 (1994).

Noboru Kaneko et al., "Inhibition of annexin V-dependent $Ca^{2+}$ movement in large unilamellar vesicles by K201, a new 1,4-benzothiazepine derivative," Elsevier Science B.V., Biochimica Et Biophysica Acta (BBA), retrieved Jan. 20, 1997; revised May 20, 1997; accepted May 26, 1997.

* cited by examiner

USE OF 1,4-BENZOTHIAZEPINE DERIVATIVES AS DRUGS FOR OVERCOMING RESISTANCE TO ANTICANCER DRUGS

This application is a 371 of PCT/JP00/03216, filed May 19, 2000, which claims foreign priority to Japan 139196/1996, filed May 19, 1999, under 35 U.S.C. 119(a)–(d).

TECHNICAL FIELD

The present invention relates to use of 1,4-benzothiazepine derivatives as a drug for overcoming a resistance to an anticancer drug or as a drug for enhancing an effect of an anticancer drug. More specifically, the present invention relates to a pharmaceutical composition containing 1,4-benzothiazepine derivatives and for overcoming a resistance to anticancer drugs and/or enhancing an effect of anticancer drugs applied to mammals including human. The present invention also relates to treatment for a cancer, and relates to a pharmaceutical composition and a pharmaceutical kit, each of which is useful particularly for treating a cancer having an acquired resistance to an anticancer drug. Further, the present invention relates to a method for treating cancer, which includes administrating an anticancer drug in combination with an agent for overcoming the resistance to the anticancer drug or an agent for enhancing the effect of the anticancer drug.

BACKGROUND ART

It is well known that when administering an anticancer drug to a cancer patient, the effect of the anticancer drug will be reduced as the administration is repeated. Along with the repeated administrations, cancer cells having the resistance to the cancer drug will appear in the living body, which always forces complicated chemotherapies for the cancer. Such a drug-resistance is generally classified into a spontaneous resistance and an acquired resistance. In a cancer treatment with an anticancer drug, a cancer cell having high sensitivity to the anticancer drug will disappear, while a cancer cell having low sensitivity to the anticancer drug will remain. Even in one cancer, both the cells having high and low sensitivities to the anticancer drug are included together. The cancer cell having high sensitivity to the anticancer drug is yielded with the acquired resistance by coming in contact with the anticancer drug. In view of clinical aspects, cancers can be classified into a first cancer group having relatively high sensitivity to anticancer drugs, such as small cell cancer, ovarian cancer and mammary cancer, and a second cancer group having lower sensitivity to anticancer drugs, such as non-small cell cancer, gastric cancer and colon cancer.

In the cell having a resistance to an anticancer drug, the following phenomenon is observed:
1) deterioration in a function of taking in drugs due to transformation in cell membrane,
2) acceleration of releasing drugs due to P-glycoprotein, multidrug-resistance associated protein (MRP) or the like,
3) degraded activity of drug activating enzyme, such as P-450,
4) enhanced activity of detoxication enzyme, such as glutathione S-transferase (GST), glutathione peroxidase (GSH-Px), DT-diaphorase, UDP-glucuronosyltransferase, metallothionein and the like,
5) increased concentration of reduced glutathione (GSH) to be involved with detoxication of various anticancer drugs, and
6) enhancement in DNA repair activity (topoisomerase).

Among cells having a resistance to an anticancer drug, a part of the cells which have acquired a resistance to a specific anticancer drug can exhibit additional resistance to another drug. This is referred to as multidrug resistance (MDR). It is known that the cell acquired the multidrug resistance develops a high amount of P-glycoprotein having a molecule weight of 170 kD. P-glycoprotein also exists in various normal cells, and is involved with various excretory mechanisms. With respect to anticancer drugs, P-glycoprotein has a pump function to release various anticancer drugs out of a cell by using ATP-energy, and functions to lower the concentration of the anticancer drug in the cell so as to allow the cell to have the acquired resistance to the anticancer drug. The releasing function of P-glycoprotein has a limited selectability for anticancer drugs so that several kinds of anticancer drugs are released out of the cell. Thus, it is believed that the cell having overdeveloped P-glycoprotein may acquire the multidrug resistance. Known cancers include one type, such as colon cancer, hepatic cancer, pancreatic cancer, or kidney cancer which has a highly developed P-glycoprotein, and another type, such as acute leukemia, malignant lymphoma or neuroblastoma, in which P-glycoprotein will be increasingly developed along with recurrences thereof, as well as breast carcinoma, head and neck cancer, lung cancer, bladder cancer, prostatic cancer, or melanoma, which has a small amount of developed P-glycoprotein.

In 1981, it was found that verapamil as a calcium antagonistic drug could overcome the multidrug resistance [Cancer Res., 41, 1967–1972, (1981)]. Thereafter, it has been verified that some calcium antagonistic drugs and calmodulin antagonistic drugs had the function of overcoming the resistance. It has also been verified that cyclosporin A as an immunosuppressive agent had the function of overcoming the resistance. It is assumed that verapamil or cyclosporin A overcomes the resistance by competing with P-glycoprotein in the site where the P-glycoprotein is bound with an anticancer drug to inhibit the function of P-glycoprotein. Further, it is also suggested that cyclosporin A has a possibility of providing the effect by affecting to drug-metabolizable enzymes represented by cytochrome P-450. The effect of the coadministration of cyclosporin A and etoposide has been clinically verified, and it has been reported that the coadministration of cyclosporin A and standard chemotherapeutics provided an excellent result in acute myelogenous leukemia and myeloma. However, these calcium antagonistic drugs and immunosuppressive agent have serious side effects caused by calcium antagonistic and immunosuppressive actions inherently involved therein, resulting in difficulty in their clinical application.

MS-209 having the following general formula is also known as a multidrug-resistance overcoming agent having a low calcium antagonistic action [Cancer Chemother. Pharmacol., 35, 271–277 (1995), Cancer Chemother. Pharmacol., 36, 361–367 (1995)]. It is believed that MS-209 overcomes the resistance by binding directly with P-glycoprotein to prevent an anticancer drug from binding with P-glycoprotein.

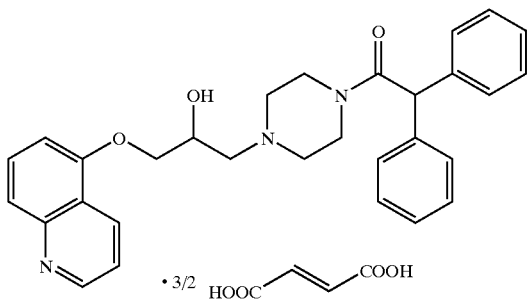

In addition, tamoxifen as a hormone drug is supposed that when used in high dose, it acts to restrain the function of P-glycoprotein by suppressing protein kinase C, and tamoxifan or toremifene is considered to use as a drug for controlling the resistance. It has been reported that the effectiveness of these drugs generally depended on the kind of anticancer drugs independently of the existence of estrogen receptor of a cancer cell, and they were effective to vinblastine, adriamycin and etoposide but were not effective to cisplatin and melphalan.

On the other hand, a cell line has been found which has no overdeveloped P-glycoprotein but exhibits the multidrug resistance to anticancer drugs including vinca alkaloid. In 1992, Cole et al successively separated c DNA corresponding to overdeveloped m RNA in doxorubicin-resistant line H69AR of pulmonary parvocellular cancer cell line H69 having no developed P-glycoprotein. They found a protein consisting of 1,531 amino acids coded by such c DNA, and called the protein as MRP (Multidrug Resistance-associated Protein) [Science, 258, 1650–1654, (1992)]. MRP is a membrane protein of 190 kD and belongs to ABC (ATP binding cassette) super family. MRP functions as a pump for releasing anticancer drugs as with P-glycoprotein. MRP is highly developed in a particular cell line, such as non-small cell lung cancer, thyroid gland cancer, glioma and neuroblastoma. It is indicated that these cancers have poor response to chemotherapy. There is also a report describing that overdeveloped MRP was often observed in chronic lymphocytic leukemia. MRP releases various anticancer drugs each having no similarity in chemical structure as with P-glycoprotein, but the resistance level of MRP is lowered as the concentration of glutathione in cells is reduced. In addition, glutathione conjugates such as leukotriene are transferred by MRP, therefore, it is possible to release anticancer drugs as hydrophilic compounds after metabolized and modified. MRP recognizes, as a substrate, glucronic acid and sulfate conjugates as well as glutathione conjugates. Further, it is believed that MRP also transfers a substrate having a multivalent negative charge, and a similarly modified heavy metal. There is some reports describing that a certain drug, such as verapamil and cyclosporin A, capable of overcoming the multidrug resistance associated with P-glycoprotein partially overcame the multidrug resistance associated with MRP. However, no distinctive drug for the multidrug resistance associated with MRP exists at present.

Recently, one glutathione-conjugate releasing pump other than MRP has been found. A cisplatin-resistance cell, KCP-4 cell, which was isolated from human nasopharyngeal cancer KB cells, exhibited about 63-fold resistance to cisplatin. The concentration of cisplatin in the KCP-4 cell was lowered, and an ATP-dependent cisplatin releasing pump was developed [Jpn. J. Cancer Bes., 85, 423–433, (1994)]. In this KCP-4 cell, the concentration of glutathione was 4.7 times higher than its parental cell line. When the concentration of glutathione was reduced down to the value equal to or less than that of the parental cell line by using a glutathione synthetase inhibitor, the resistance to cisplatin is lowered to approximately half of the initial level. In the KCP-4 cell, MRP develops neither protein nor mRNA. Thus, it is believed that there is another glutathione-conjugate releasing pump different from MRP [BBRC, 256, 158–165, (1996)]. A cMOAT gene isolated from the KCP-4 cell has a homogeny with MRP. Comparing three cisplatin-resistant cells of KCP-4, PC 5 and T 24 with the corresponding parental cell lines, respectively, 4 to 6-fold mRNA is developed in the cMOAT. Thus, it is believed that cMOAT is a protein involved with the resistance to cisplatin.

A resistance mechanism by detoxifying anticancer drugs is also known. Glutathione S-transferase (GST) is one of detoxication enzymes. GST exists mostly in liver and is widely distributed over other organs, mainly as a dimer in the cytoplasm. Many molecular types are known, which includes molecular types involved with glutathione (GSH) conjugating activity (GST activity) and glutathione peroxidase (GSH-Px) activity as well as molecular types participating in metabolism of leukotriene and prostaglandin. Many alkalizing agents such as nitrogen mustard are detoxified by receiving GSH conjugation. Cisplatin and VP-16 are detoxified by GSH chelation and GSH conjugation, respectively [Biochem. Soc. Transact., 15, 728–730, (1987)].

A drug resistance yielded by metallothionein is also known. Metallothionein was found in horse kidney as a cadmium-binding protein, and is a relatively small protein having a molecular weight of 6000. Metallothionein has a characteristic structure including cysteine which accounts for approximately ⅓ of total constitutive amino acids and has no S—S binding. In 1981, Bakka et al discovered that cadmium-resistant cells containing a high concentration of metallothionein also exhibited the resistance to cisplatin, and suggested that metallothionein had a possibility of acting as a resistance factor to cytotoxicity of cisplatin [Toxicol. Appl. Parmacol., 61, 215–226, (1981)]. Further, it was clarified that a cell isolated from prepared metallothionein-gene-deficient mice had a higher sensitivity to cisplatin [Cancer Res., 55, 2021–2023, (1995)]. In a study using mice with cancer, it has been verified that the anticancer effect not only of cisplatin but also of adriamycin, bleomycin, cyclophosphamide and melphalan were significantly reduced by increasing the concentration of metallothionein in the cancer tissue twice through administering zinc. It is assumed that the resistance to plural anticancer drugs can be acquired due to increased concentration of metallothionein. Amino acid derivatives of propargyl glycine for inhibiting metallothionein synthesis are being studied, but are now too toxic for clinical use.

Topoisomerase is an enzyme acting on alternating DNA topology. It is known topoisomerase having type I and II, wherein adriamycin and etoposide inhibit the type II, and camptothecin inhibit the type I. It is verified that a camptothecin-resistant cancer cell includes the structure of topoisomerase having developed point mutation.

As to a multidrug-resistance overcoming drug, Japanese Patent Laid-Open Publication No. Hei 8-92218 describes a compound represented by the following general formula:

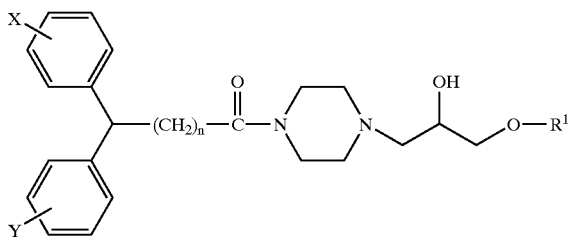

(where X and Y represent hydrogen atom or halogen atom, n represents an integer of 1–4, $R^1$ represents monocyclic or bicyclic aromatic chain which may include halogen atom, alkyl group with C atom numbers that vary from 1–4, alkyloxy group with C atom numbers that vary from 1–4, or nitrogen atom which maybe substituted with nitro group.)

Japanese Patent Laid-Open Publication No. Hei 8-509223 (WO 94/24107, U.S. Pat. No. 5,643,909, U.S. Pat. No. 5,654,304, European Patent 695,293) describes a compound represented by the following general formula:

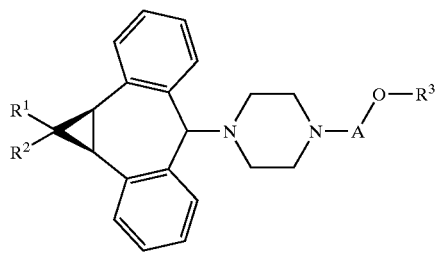

[where A is —$CH_2$—$CH_2$—, $CH_2$—$CHR^a$—$CH_2$—, or —$CH_2$—$CHR^a$—$CHR^b$—$CH_2$—(where one of $R^a$ or $R^b$ is H, OH, or lower alkyloxy, and the other is H), $R^1$ and $R^2$ are H, F, Cl or Br; and $R^3$ is heteroaryl or phenyl optionally substituted with a substituent selected from the group consisting of F, Cl, Br, $CF_3$, CN, $NO_2$ or $OCHF_2$], and Japanese Patent Laid-Open Publication No. Hei 10-7660 (U.S. Pat. No. 5,700,826, European Patent 812829) describes a compound represented by the following general formula:

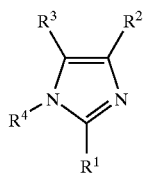

(where $R^1$ represents substituted alkyl, substituted alkenyl or the like, $R^2$ and $R^3$ represent aryl or the like, and $R^4$ represents hydrogen, substituted alkyl, substituted alkenyl or the like). However, the above publications do not describe any 1,4-benzothiazepine derivatives according to the present invention.

As to compounds according to the present invention, Japanese Patent Laid-Open Publication No. Hei 4-230681 (International Publication WO 92/12148, European Patent 565721, U.S. Pat. No. 5,416,066) describes 1,4-benzothiazepine derivatives represented by the following general formula or pharmaceutically acceptable salts thereof, and a manufacturing method of compounds thereof:

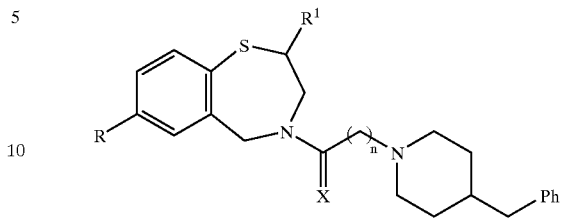

[where R represents hydrogen atom or a lower alkoxy group with C atom numbers that vary from 1–3; $R^1$ represents hydrogen atom, a lower alkoxy group with C atom numbers that vary from 1–3, a substituted phenyl group (where the substituent group is a hydroxyl group or a lower alkoxy group with C atom numbers that vary from 1–3),

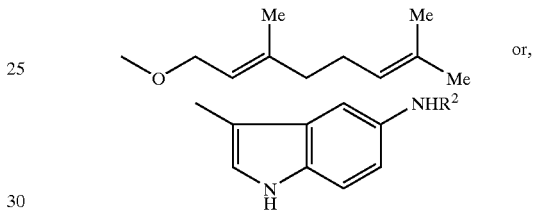

(where $R^2$ represents an acyl group with C atom numbers that vary from 1–3), X represents oxygen or $H_2$; n represents 1 or 2; and Ph represents a phenyl group].

Japanese Patent Laid-Open Publication No. Hei 4-230681 describes that the myocardium of a myocardial infarction patient includes two necrosis forms [Static Cell Death (SD) and Kinetic Cell Death (KD)], and KD is a dominant cause of myocardial infarction of human. This publication includes a description that the inventive compound has a KD suppressing effect and is thereby useful as drugs for preventing and treating myocardial infarction. However, there is no description about overcoming the resistance to anti-cancer drugs.

Kaneko, one of the inventors of the present invention, has reported that the following compounds had an intracellular calcium blocking effect [Drug Dev. Res., 33, 429–438 (1994)], and is useful as a calcium channel inhibitor [J. Mol. Biol., 274, 16–20 (1997)].

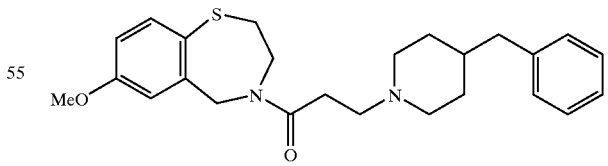

However, the above documents include no description about the effect of overcoming the resistance to anticancer drugs, which is a subject matter of the present invention.

It is known that conventional calcium antagonistic drugs such as verapamil inhibit P-glycoprotein [Cancer Res., 49, 5002–5006 (1989)]. On the other hand, there is a report describing that in an experimental test using a B16a cell, which is a melanin-deficient cell of a B16 cell, and a B16a-Pt cell line, which is a cisplatin-resistant mutant of the B16a cell, nifedipine as a calcium antagonistic drug enhances the antitumor effect of cisplatin, but verapamil, diltiazem, nimodipine and nicardipine as well as trifluoperazine and calmidazilium as a calmodulin antagonistic drug do not exhibit any significant enhanced antitumor effect [Cancer Res., 49, 2844–2850 (1989)]. There is also a report describing that in an experimental test using a GB-1 cell as a human glioblastoma cell and a U87-GM cell, none of verapamil, diltiazem, nimodipine, nicardipine, benidipine, nilvadipine and nisoldipine enhances any significant antitumor effect of cisplating [J. Neurosurg., 82, 469–474 (1995)].

In Drug Dev. Res., 33,429–438(1994), there is a description that diltiazem, a 1,5-benzothiazepine compound, and the following compound, 1,4-benzothiazepine, are analogous to each other,

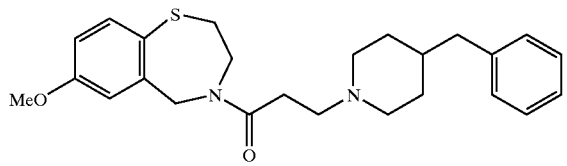

and diltiazem does not enhance any significant antitumor effect of cisplatin. As long as the description of this report, it is assumed that the compounds according to the present invention would not exhibit any effect of overcoming the resistance to cisplatin. However, the compounds according to present invention, which is represented by the general formula [1], have an extremely strong effect of overcoming the resistance to platinum complex such as cisplatin, as is clear from the aftermentioned example.

A tumor cell acquires the resistance to platinum complex such as cisplatin by a mechanism, such as reduced accumulation of the platinum complex in the tumor cell, detoxication yielded by glutathione, metallothionein and the like, and enhanced function of modifying damaged DNA [Jpn. J. Cancer Res., 79, 301–304 (1988), J. Biol. Chem., 265, 4296–4301 (1990), Jpn. J. Cancer Res., 81, 527–535 (1990), Br. J. Cancer, 67, 1171–1176 (1993), Cancer Res., 53, 5225–5232 (1993)], Cancer Res., 53, 3694–3699 (1993), Pharmacol. Ther., 52, 385–406 (1991)]. Thus, it may be difficult to overcome the resistance to cisplatin only by inhibiting P-glycoprotein. The compounds according to the present invention, which is represented by the general formula [I], overcome the resistance supposedly by a different mechanism from that in the conventional calcium antagonistic drugs, but the detail has not been known yet. Further, the compounds according to the present invention, which is represented by the general formula [I], surprisingly have a strong effect of overcoming the resistance to anticancer drugs such as taxol and adriamycin.

DISCLOSURE OF THE INVENTION

It is therefore an object of the present invention to provide a drug for overcoming an resistance to an anticancer drug and a drug for enhancing the effect of an anticancer drug, which are used for mammals such as human.

It is another object of the present invention to provide a pharmaceutical composition and a pharmaceutical kit, which are useful for treating cancer in mammals including human.

It is still another object of the present invention to provide a drug for overcoming a resistance to an anticancer drug, a drug for enhancing an effect of an anticancer drug, a pharmaceutical composition, and a pharmaceutical kit, which are useful for treating cancer having the developed resistance to the anticancer drug.

It is yet another object of the present invention to provide a method for treating cancer, which is effective to cancers including one having a developed resistance to an anticancer drug.

In order to achieve the above objects, the inventors have continuously researched, and discovered that a specific compound represented by the following general formula [I] surprisingly have a function of overcoming a resistance to an anticancer drug and enhancing the effect of the anticancer drug, with low toxicity. Finally, the inventors have accomplished the present invention.

All of the conventional drugs for overcoming the resistance have been drugs for overcoming the resistance against so-called MDR associated with P-glycoprotein and multi-drug-resistance associated protein (MRP). As to calcium antagonistic drugs, it is reported that the effect of verapamil for overcoming the resistance is also associated with MDR, and verapamil has no effect on the resistance to cisplatin in an animal test. In addition, there is a report describing that a clinical test on MDR for children was attempted, but discontinued because of undesirably lowered blood pressure (bradycardia). It seems that the mechanism of the resistance to cisplatin is supposedly different from that of MDR, and thus it is a new and surprising knowledge that the compound according to the present invention, which is represented by the following general formula [I], has an ability of overcoming the resistance to cisplatin.

The present invention relates to a pharmaceutical composition for overcoming a resistance to an anticancer drug or enhancing an effect of an anticancer drug, which comprise a compound represented by the following formula [I] as an active ingredient. The detail is shown in the following (1)–(27):

(1) A pharmaceutical composition for overcoming a resistance to an anticancer drug, comprising a compound represented by the following general formula [I] or a pharmaceutically acceptable salt or prodrug thereof, together with a pharmaceutically acceptable carrier;

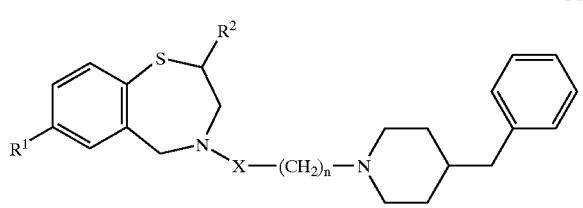

[where $R^1$ represents hydrogen atom or lower alkoxy group; $R^2$ represents hydrogen atom, lower alkoxy group, or phenyl group (wherein said phenyl group may be substituted with 1–3 substituents selected from the group consisting of hydroxyl group and lower alkoxy group), or a group represented by the following formula,

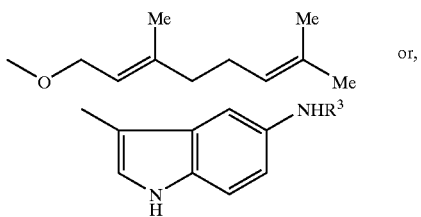

(where R³ represents acyl group); X represents —CO— or —CH₂—; and n represents 1 or 2].

(2) A pharmaceutical composition described in the above (1), wherein said compound is a 4-[3-(4-benzylpiperidine-1-yl)propionyl]-7-methoxy-2,3,4,5-tetrahydro-1,4-benzothiazepine, namely 4-[3-[1-(4-benzyl)piperidinyl]propionyl]-7-methoxy-2,3,4,5-tetrahydro-1,4-benzothiazepine, or a pharmaceutically acceptable salt or prodrug thereof.

(3) A pharmaceutical composition described in the above (1) or (2), wherein said anticancer drug is platinum complex, antitumor substance derived from a plant, or antitumor antibiotic.

(4) A pharmaceutical composition described in the above (3), wherein said anticancer drug is cisplatin, carboplatin, nedaplatin, adriamycin or taxol.

(5) A pharmaceutical composition for enhancing an effect of an anticancer drug, comprising a compound represented by the above general formula [I] or a pharmaceutically acceptable salt or prodrug thereof, together with a pharmaceutically acceptable carrier.

(6) A pharmaceutical composition described in the above (5), wherein said compound is 4-[3-(4-benzylpiperidine-1-yl)propionyl]-7-methoxy-2,3,4,5-tetrahydro-1,4-benzothiazepine, or a pharmaceutically acceptable salt or prodrug thereof.

(7) A pharmaceutical composition described in the above (5) or (6), wherein said anticancer drug is platinum complex, antitumor substance derived from a plant, or antitumor antibiotic.

(8) A pharmaceutical composition described in the above (7), wherein said anticancer drug is cisplatin, carboplatin, nedaplatin, adriamycin or taxol.

(9) A pharmaceutical composition for reducing a resistance of cancer to an anticancer drug, comprising a compound represented by the above general formula [1] or a pharmaceutically acceptable salt or prodrug thereof, together with a pharmaceutically acceptable carrier.

(10) A pharmaceutical composition for increasing a sensitivity of cancer to an anticancer drug, comprising a compound represented by the above general formula [1] or a pharmaceutically acceptable salt or prodrug thereof, together with a pharmaceutically acceptable carrier.

(11) A pharmaceutical composition comprising a compound represented by the above general formula [I] or a pharmaceutically acceptable salt or prodrug thereof, and an anticancer drug.

(12) A method for overcoming a resistance to an anticancer drug, comprising administering an effective amount of a compound represented by the above general formula [I] or a pharmaceutically acceptable salt or prodrug thereof.

(13) A method for enhancing an effect of an anticancer drug, comprising administering an effective amount of a compound represented by the above general formula [I] or a pharmaceutically acceptable salt or prodrug thereof.

(14) A method for reducing a resistance of cancer to an anticancer drug, comprising administering an effective amount of a compound represented by the above general formula [1] or a pharmaceutically acceptable salt or prodrug thereof.

(15) A method for increasing a sensitivity of cancer to an anticancer drug, comprising administering an effective amount of a compound represented by the above general formula [1] or a pharmaceutically acceptable salt or prodrug thereof.

(16) A method for treating a cancer, comprising administering an effective amount of a compound represented by the above general formula [1] or a pharmaceutically acceptable salt or prodrug thereof, together with an effective amount of an anticancer drug.

(17) A method for treating a cancer having a resistance to an anticancer drug, comprising administering an effective amount of a compound represented by the above general formula [1] or a pharmaceutically acceptable salt or prodrug thereof, together with an effective amount of an anticancer drug.

(18) A use of a compound represented by the above general formula [I] or a pharmaceutically acceptable salt or prodrug thereof, for manufacturing a drug for overcoming a resistance to an anticancer drug.

(19) A use of a compound represented by the above general formula [I] or a pharmaceutically acceptable salt or prodrug thereof, for manufacturing a drug for enhancing an effect of an anticancer drug.

(20) A use of a compound represented by the above formula [1] or a pharmaceutically acceptable salt or prodrug thereof, for manufacturing a drug for reducing a resistance of cancer to an anticancer drug.

(21) A use of a compound represented by the above general formula [1] or a pharmaceutically acceptable salt or prodrug thereof, for manufacturing a drug for increasing a sensitivity of cancer to an anticancer drug.

(22) A commercial package comprising a pharmaceutical composition described in any one of the above (1) to (4), and a description about said pharmaceutical composition in which said pharmaceutical composition may or should be used for overcoming a resistance to an anticancer drug.

(23) A commercial package comprising a pharmaceutical composition described in any one of the above (5) to (8), and a description of said pharmaceutical composition in which said pharmaceutical composition may or should be used for enhancing an effect of an anticancer drug.

(24) A commercial package comprising a pharmaceutical composition described in any one of the above (1) to (4), and a description of said pharmaceutical composition in which said pharmaceutical composition may or should be used for reducing a resistance of cancer to an anticancer drug.

(25) A commercial package comprising a pharmaceutical composition described in any one of the above (1) to (4), and a description of said pharmaceutical composition in which said pharmaceutical composition may or should be used for increasing a sensitivity of cancer to an anticancer drug.

(26) A pharmaceutical kit for treating a cancer, comprising two kinds of drugs, wherein a first drug is a drug for overcoming a resistance to an anticancer drug, which includes a compound represented by the above general formula [1] or a pharmaceutically acceptable salt or prodrug thereof, wherein a second drug is said anticancer drug.

(27) A pharmaceutical kit for treating a cancer, comprising two kinds of drugs, wherein a first drug is a drug for enhancing an effect of an anticancer drug, which includes a compound represented by the above general formula [1] or a pharmaceutically acceptable salt or prodrug thereof, wherein a second drug is said anticancer drug.

Preferably, the compound represented by the general formula [I] is 4-[3-(4-benzylpiperidine-1-yl)propionyl]-7-methoxy-2, 3, 4, 5-tetrahydro-1,4-benzothiazepine.

The anticancer drug is preferably platinum complex, antitumor substance derived from a plant, or antitumor antibiotics, and more preferably cisplatin, carboplatin, nedaplatin, adriamycin or taxol.

DETAILED DESCRIPTION OF THE INVENTION

For the purpose of describing the present invention, terms used herein will be defined as follows.

The term "a drug for overcoming a resistance to an anticancer drug or an anticancer-drug-resistance overcoming drug" or "a pharmaceutical composition for overcoming a resistance to an anticancer drug or an anticancer-drug-resistance overcoming pharmaceutical-composition" refers to a drug which has no carcinostatic activity itself but has a function of reducing a resistance of cancer cells to an anticancer drug. In other words, it means a drug having a function for increase a sensitivity to an anticancer drug of cancer cells having an acquired resistance to the anticancer drug. In this case, the increase of the sensitivity means not only to increase an effect of an anticancer drug to anticancer-drug resistant cells in a higher level than that to anticancer-drug sensitive cells but also to increase the effect of the anticancer drug to the anticancer-drug resistant cells in approximately the same level as that to the anticancer-drug sensitive cells. Further, another term equivalent to "overcoming a resistance" may include "restraining or inhibiting a resistance", "releasing resistance", "releasing tolerance" or "increasing or enhancing a sensitivity".

The term "a drug for enhancing a effect of an anticancer drug or an anticancer-drug-effect enhancing drug" or "a pharmaceutical composition for enhancing an effect of an anticancer drug or an anticancer-drug effect enhancing pharmaceutical-composition" refers to a drug which has no carcinostatic activity itself but enhances an activity of an anticancer drug, i.e. an carcinostatic effect of an anticancer drug itself, by administering it together with the anticancer drug. In this case, the term "enhancing or increasing" means not only to increase an effect level of an anticancer drug to anticancer-drug resistant cells in an equal to or higher than that to anticancer-drug sensitive cells but also to increase a sensitivity of cancer cells, which have not acquired any resistance, to the anticancer drug.

Therefore, by using the anticancer-drug-resistance overcoming drug or the anticancer-drug-effect enhancing drug according to the present invention, a sensitivity of cancer cells having an acquired resistance to an anticancer drug can be increased, and thereby the dosage of the anticancer drug can be reduced or the intervals of administration of the anticancer drug can be extended.

The term "a method for overcoming a resistance to an anticancer drug" means a method for reducing a resistance of cancer cells to an anticancer drug, i.e. a method for increasing a sensitivity of cancer cells, which have acquired a resistance to an anticancer drug, to the anticancer drug.

The term "a method for enhancing or increasing an effect of an anticancer drug" means a method for enhancing or increasing an activity of an anticancer drug, in other word, a method for enhancing or increasing an carcinostatic effect of an anticancer drug itself.

The term "lower alkoxy group" includes straight or branched chain alkoxy group with one to six carbon atoms, such as methoxy, ethoxy, propoxy, isopropoxy, butoxy, tert-butoxy, pentyloxy, tert-pentyloxy or hexyloxy group, more preferably, methoxy, ethoxy, propoxy or isopropoxy group of one to three carbon atoms, most preferably, methoxy group.

The term "acyl group" includes formyl group with one carbon atom; alkanoyl group with two to six carbon atoms, such as acetyl, propionyl, butyryl, or pivaloyl group; or aroyl group, such as benzoyl group which may have substituents with one to three carbon atoms on aryl group. Preferably, it is formyl, acetyl, pivaloyl or benzoyl group.

The term "Salt" of the compound represented by the general formula [I] includes any pharmaceutically acceptable salts, preferably, any pharmaceutically acceptable acid addition salts including, for example, but not limited to, an inorganic acid addition salt, such as hydrochloride, hydrobromide, sulfate, phosphate or nitrate; an organic acid addition salt, such as acetate, propionate, succinate, glycolate, lactate, malate, oxalate, tartrate, citrate, maleate, fumarate, methanesulfonate, benzenesulfonate, p-toluenesulfonate or ascorbate; or an amino acid addition salt, such as aspartate or glutamate. Further, it may be a salt containing water or hydrates.

The term "Prodrug" of the compound represented by the general formula [I] includes any derivatives of the compound according to the present invention, each of which has chemically or metabolically degradable group and exhibits a pharmaceutical activity by hydrolysis or solvolysis, or by degradation under a physiological condition.

The term "Anticancer drug" includes, but not limit to, alkalizing agent, such as busulfan, carboquone, cyclophosphamide, ifosfamide, melfaran, nitrogen mustard, thiotepa, uracil mustard, carmustine (BCUN), nimustine hydrochloride (ACNU), estramustine phosphate; antimetabolite, such as azathioprine, ancitabine, carmofur, doxifluridine, fluorouracil (5-FU), mercaptopurine (6-MP), thioinosine, tegafur, cytarabine (Ara-C), methotrexate (MTX), hydroxycarbamide, cytarabine ocfosfate, pentostatin; antitumor antibiotics, such as dactinomycin, mitomycin C, bleomycin (BLM), daunorubicin, adriamycin (doxorubicin), neocarzinostatin (NCS), idarubicin hydrochloride; antitumor substance derived from a plant, such as etoposide (VP-16), teniposide, vindesine, vincristine, vinblastine, taxol (paclitaxel), irinotecan hydrochloride; platinum complex, such as cisplatin (CDDP), carboplatin (CBDCA), nedaplatin (NDP); hormone drug, such as predonisone, prednisolone, testosterone, estramustine, norethisterone, goserelin acetate, leuprorelin acetate, toremifene citrate, fadrozole hydrochloride, tamoxifen; anthracyclinic compound, such as mitoxantrone (MXT). A preferred anticancer drug includes platinum complex, such as cisplatin, carboplatin, nedaplatin; antitumor antibiotics, such as dactinomycin, mitomycin C, bleomycin, daunorubicin, adriamycin, neocarzinostatin, idarubicin hydrochloride; and antitumor substance derived from a plant, such as etoposide, teniposide, vindesine, vincristine, vinblastine, taxol, irinotecan hydrochloride. More preferably, it includes cisplatin, carboplatin, nedaplatin, adriamycin, and taxol, and most preferably, cisplatin.

The most preferred category of the anticancer drug is platinum complex, and antitumor substance derived from a plant is the second place.

In the compound according to the present invention, which is represented by general formula [I], $R^1$ is preferably a lower alkoxy group with one to three carbon atoms, most preferably a methoxy group. $R^2$ is preferably a lower alkoxy group with one to three carbon atoms or a hydrogen atom, most preferably a hydrogen atom. X is preferably —CO—, and n is preferably 2.

Preferably, the compound represented by the general formula [I] or the salt thereof may be used as an active ingredient in the anticancer-drug-resistance overcoming drug, the anticancer-drug-effect enhancing drug and the pharmaceutical composition of the present invention.

The compound according to the present invention, which is represented by the general formula [I], may be made based on the method described in Japanese Patent Laid-Open Publication No. Hei 4-230681 (International Publication WO-92/12148, European Patent 565721, U.S. Pat. No. 5,416,066).

The compound according to the present invention, which is represented by the general formula [I], has an effect excellent in overcoming a resistance to an anticancer drug and enhancing an effect of an anticancer drug. Specifically, by administering the anticancer-drug-resistance overcoming drug or the anticancer-drug-effect enhancing drug together with an anticancer drug, the carcinostatic action of the anticancer drug may be effectively performed against cancer cells having the acquired resistance to anticancer drug. When used as the anticancer-drug-resistance overcoming drug or the anticancer-drug-effect enhancing drug, the compound of the present invention is typically administered systemically or topically, through oral or parenteral route. Parenteral administration includes intravenous (including drip infusion), intra-arterial, intramuscular, subcutaneous, intraperitoneal, intrathoracic, intravesical, intraspinal, percutaneous, mucosal, intrarectal and intratumoral administration. The anticancer-drug-resistance overcoming drug or the anticancer-drug-effect enhancing drug of the present invention may be administered simultaneously with, or before or after administration of an anticancer drug, or may be administered during a cessation of the anticancer drug in some cases. An administration route of the anticancer-drug-resistance overcoming drug or anticancer-drug-effect enhancing drug may be the same as or different from that of an anticancer drug.

The anticancer-drug-resistance overcoming drug or the anticancer-drug-effect enhancing drug of the present invention may be used by administering together with an anticancer drug in treating cancer (malignant tumor), such as lung cancer (non-small cell lung cancer, small cell lung cancer), large intestine cancer (rectum cancer, colon cancer), small intestine cancer, gastric cancer, esophageal cancer, hepatic cancer, pancreatic cancer, malignant melanoma, renal cancer, bladder cancer, uterine cancer (cervical cancer, corpus uteri cancer), ovarian cancer, mammary cancer, osteosarcoma, malignant lymphoma, prostatic cancer, leukemia (acute leukemia, chronic leukemia), myeloma, neuroblastoma, head and neck cancer, skin cancer, and orchidoncus, in mammals including human.

The term "administrating together with" in the present invention means administering two kinds of drugs simultaneously, continuously or at intervals. The two kinds of drugs may be administered as a mixture or as separate drugs. When administering as separate drugs, each administering route may be or may be not the same.

The dosage of the compound represented by the general formula [I] or the salt or prodrug thereof is varied depending on age, weight, symptoms, therapeutic effects, administration route, treatment time and the like. Generally, it is administered orally or parenterally at an amount in the range of 0.01 mg to 1 g per adult and one to several times a day.

A dosage of an anticancer drug administered together with the compound may be equal to or less than that for usual cancer treatments. A route of administration for the anticancer drug administered together with the compound may also be the same as that used for usual cancer treatments.

Further, a pharmaceutical composition containing the compound represented by the general formula [I] or the salt or prodrug thereof and an anticancer drug may be prepared and administered. In the composition, the weight ratio of the compound represented by the general formula [I] or the salt thereof or prodrug of the same to the anticancer drug may be arranged, but not limit to, in the range of 1:100 to 100:1.

According to the present invention, there is provided a pharmaceutical kit for treating cancer, including two drugs. In the pharmaceutical kit for treating cancer of the present invention, a first drug is a drug for overcoming a resistance of an anticancer drug or for enhancing an effect of an anticancer drug, which contains a compound represented by the general formula [I] or the salt or prodrug thereof, and a second drug is the anticancer drug. These two drugs may be used for treating cancer, especially cancer having an acquired resistance to the anticancer drug by administering the first drug together with the second drug. The anticancer-drug-resistance overcoming drug or anticancer-drug-effect enhancing drug as the first drug may be administered simultaneously with, or before or after administration of the anticancer drug as the second drug, or may be administered during the cessation of the anticancer drug in some cases. An administration route of the anticancer-drug-resistance overcoming drug or anticancer-drug-effect enhancing drug may be or may be not the same as that of the anticancer drug.

When prepared as a solid composition for oral administration, the compound of the present invention may be formed in any suitable dosage form including tablet, pill, powder, and granule. In such a solid composition, one or more active substances are mixed with at least one of inactive diluent, dispersant, and adsorbent, such as lactose, mannitol, glucose, hydroxypropylcellulose, microcrystalline cellulose, starch, polyvinyl pyrrolidone, magnesium aluminate metasilicate, or silicic acid anhydride powder. In addition, the composition may be mixed with additives other than diluents based on common manner in the art.

When prepared as tablets or pills, they may be coated, if necessary, with one or more films of gastric or enteric coating substance, such as saccharose, gelatin, hydroxypropylcellulose or hydroxymethylcellulose phthalate. Further, they may be capsuled with substance, such as gelatin or ethyl cellulose.

When prepared as a liquid composition for oral administration, the compound of the present invention may be formed in any suitable dosage form including pharmaceutically acceptable emulsion, resolvent, suspension, syrup, elixir or the like. A suitable diluent may include purified water, ethanol, vegetable oil, or emulsifier. Further, this composition may be mixed with an auxiliary agent other than diluent, such as humectant, suspension, sweetening agent, flavor agent, fragrance agent, or antiseptic agent.

When prepared as injection for parenteral administration, axenic aqueous or non-aqueous solution agents, solubilizing agents, suspensions or emulsifiers are used. Aqueous solution agent, solubilizing agents or solution agent may include water for injection, distilled water for injection, physiological saline; cyclodextorin and derivatives thereof, organic amines, such as triethanolamine, diethanolamine, monoethanolamine, and triethylamine, inorganic alkali solution or the like.

For example, propylene glycol, polyethylene glycol, vegetable oils such as olive oil, or alcohols such as ethanol, may be used for preparing as the water-soluble solution. Further, a surface-active agent (mixed micelle formation), such as polyoxyethylene hydrogenated castor oil or sucrose fatty acid ester, or lecithin or hydrogenated lecithin (liposome formation) may be used for preparing as the solubilizing agent. Further, the compound of the present invention may be prepared as an emulsion drug comprising water insoluble resolvent such as vegetable oils, and lecithin, polyoxyethylene hydrogenated castor oil or polyoxyethylene polyoxypropylene glycol.

Alternately, for parenteral administration, the composition may be formed in lotion, liniment such as ointment, suppository, or pessary, which contains one or more active substances and is prepared by well-known processes.

EXAMPLE

Examples of the compound of the present invention will now be described more specifically.

As a prepared compound, 4-[3-(4-benzylpiperidine-1-yl)propionyl]-7-methoxy-2,3,4,5-tetrahydro-1,4-benzothiazepine (hereinafter referred to as compound I) was used.

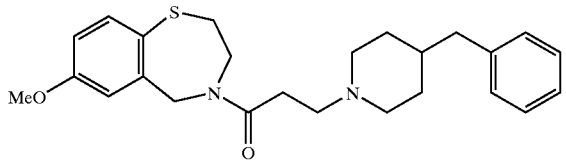

Example 1

| Injection | |
|---|---|
| compound 1 | 10 mg |
| D-sorbitol | 1000 mg |
| citric acid | 10 mg |
| sodium hydroxide | optimum dose |
| add water for injection to | 20.0 ml. |

D-sorbitol and citric acid were dissolved in sufficient water for injection. The compound 1 was dissolved into the resulting solution and pH of the solution was adjusted to 3.2–3.3 by sodium hydroxide. While agitating, the rest of water for injection was added. The solution was filtered to fill in a 20.0 ml ampule and enclosed. Then, the contents in the ampule were sterilized by using an autoclave.

Example 2

A pharmaceutical kit for treating cancer was prepared which includes the following two drugs:
a first drug the injection prepared in the example 1
a second drug cisplatin injection 20.0 ml (0.5 mg/ml)

The effect of the compound of the present invention will be described more specifically hereinafter. The compound 1 was used as a test compound.

Example 3

Function of Test Compound for Enhancing Sensitivity to Anticancer Drug in Non-Small Cell Lung Cancer Cell Line having Cisplatin Resistant.

PC-14 as a human non-small cell lung cancer cell line and PC-14/CDDP as a cisplatin tolerant cell line thereof were used to examine an effect of overcoming each resistance to cisplatin, carboplatin, nedaplatin and taxol. PC-14 and PC-14/CDDP were made into a single cell in BPMI 1640 medium by trypsinization or by using a cell scraper, and prepared a cell suspension of 100 cells per 15 $\mu$l. The compound 1 dissolved in dimethyl sulfoxide was added therein to make final concentration of 10 $\mu$m, and then the resulting liquid was poured into a 96-perforated plate at 150 $\mu$l per well. An anticancer drug was dissolved in sterilized distilled water. The resulting liquid of 150 $\mu$l per well was poured into the first row to transfer in turn from the second row to the next rows by 150 $\mu$l for each raw so as to form two-fold dilution rows. A group without the cells was prepared as a negative control, and a group without the anticancer drug and the compound I was prepared as a positive control. After culturing at 37° C. under carbon dioxide having a concentration of 5% and saturated vapor for 96 hours, an MTT [3-(4,5-dimethylthiazol-2-yl)-2,5-diphenyltetrazolium bromide] reagent of 20 $\mu$l dissolved in D-PBS (−) at a concentration of 5 mg/ml was added to each of the groups, and the resulting liquid was cultured for another 4 hours at 37° C. After the completion of the culture, the entire plate was centrifuged, and the supernatant was removed. Dimethyl sulfoxide of 200 $\mu$l was added to dissolve formazan crystal generated by enzyme activities of mitochondria in the cells. Then, absorbed light of 562–630 nm was determined by using a multiplate reader. Given that the average growth rate of the negative control is 0% and the average growth rate of the positive control is 100%, a dose-growth curve was plotted to calculate 50° C. cell growth inhibiting concentration ($IC_{50}$). The result is shown in Table 1.

TABLE 1

| | PC-14 | | PC-14/CDDP | |
|---|---|---|---|---|
| anticancer drug | without compound 1 ($\mu$M) | with compound 1 ($\mu$M) | without compound 1 ($\mu$M) | with compound 1 ($\mu$M) |
| cisplatin | 2.40 ± 1.05 | 1.77 ± 0.89 (0.73) | 18.6 ± 2.83 (7.87) | 2.16 ± 1.12 (0.90) |
| carboplatin | 37.1 ± 10.8 | 29.5 ± 11.3 (0.80) | 143 ± 39.1 (3.85) | 26.1 ± 7.78 (0.70) |
| nedaplatin | 7.10 ± 1.53 | 4.36 ± 1.53 (0.61) | 25.9 ± 8.12 (3.64) | 4.16 ± 1.28 (0.59) |
| taxol | 1.132* | 0.663* (0.50) | 5.295* (4.68) | 1.728* (1.53) |

(n = 3, mean ± SE, *n = 1)

Each figure in parentheses represents the resistance to $IC_{50}$ for the parental cell line (PC-14) without the compound 1.

As is apparent from the above result, the compound 1 shows the effect of reducing the resistance to and increasing the sensitivity to cisplatin, carboplatin, nedaplatin and taxol in the cisplatin resistant lung cancer cell line (PC-14/CDDP).

Example 4

Function of Test Compound for Enhancing Effect of Anticancer Drug in Human Leukemia Cell Line having Adriamycin Resistant.

K562 as a human promyelocytic leukemia cell line and K562/ADM as an adriamycin resistant cell line thereof were used to examine the effect of overcoming the resistance to adriamycin. The same process as the example 3 except using K562 and K562/ADM for cancer cells and adriamycin for an anticancer drug was carried out to calculate 50% cell growth inhibiting concentration ($IC_{50}$). The result is shown in Table 2.

TABLE 2

| K562 | | K562/ADM | |
|---|---|---|---|
| without compound 1 | with compound 1 | without compound 1 | with compound 1 |
| 0.008 µM | 0.004 µM (0.50) | 1.1525 µM (144) | 0.1656 µM (20.7) |

(n = 1)

Each figure in parentheses represents the resistance to $IC_{50}$ of the parental cell line (K562) without the compound 1.

As is apparent from the above result, the compound 1 shows the effect of reducing the resistance to and increasing the sensitivity to adriamycin in the adriamycin resistant lung cancer cell line (K562/ADM).

Example 5

Function for Enhancing Inhibit Tumor Cell Growth Effect of Cisplatin in Model of Nude Mice with Cancer.

Female nude mice BALB/c nu/nu (6-week-old) were implanted subcutaneously in each back with $2 \times 10^7$ of PC-14/CDDP and the parental cell line PC-14 suspended in physiological saline, then the progress of tumor were observed. On the 7th day from the implantation, tumor condition was checked to select and randomize testable individuals not to cause any deviation, and the selected mice were then divided into a control group and a test group. After each tumor volume was determined based on the formula: (tumor short diameter)$^2$×(tumor long diameter), administration of drug was started on the seventh day.

The compound 1 was used as a test compound, 1.2 mg of which was dissolved in 0.05 ml of dimethyl sulfoxide, and then combined with 0.95 ml of 5% sorbitol-0.2% citric acid 1 hydrate solution (pH3.3) to make uniform solution.

Cisplatin was used as an anticancer drug, and was dissolved in distilled water to prepare 1.6 mg/ml solution.

The administration process is carried out by simultaneous intravenous injections of 0.05 ml of the test compound and 0.05 ml of the anticancer-drug solution once a day on the 7th, 11th, 15th day after the tumor implantation. For the control group, 0.1 ml of physiological saline was administered by intravenous injection, and for the group to be administered only the anticancer drug, 0.05 ml of the anticancer-drug solution and 0.05 ml of physiological saline were administered by intravenous injection. One dose of the test compound was 3 mg/kg, and one dose of the anticancer drug was 4 mg/kg. During the administration of the drug, physical status of the whole body of the mice was observed, and the weight and the long/short lengths of tumor were measured. Tumor growth rate (GR) and effect of inhibiting cancer (lowest T/C) were calculated based on the following formulas, respectively. The result is shown in Table 3.

$$\text{tumor growth rate}(GR) = \frac{\text{tumor volume on the 21th day after tumor implantation}}{\text{tumor volume on the 7th day after tumor implantation}} \times 100(\%)$$

$$\text{effect of tumor inhibiting}(\text{lowest } T/C) = \frac{\text{lowest volume of tumor of treated group during treatment}}{\text{volume of tumor of control group}} \times 100(\%)$$

TABLE 3

| | PC-14 | | PC-14/CDDP | |
|---|---|---|---|---|
| | without compound 1 | with compound 1 | without compound 1 | with compound 1 |
| GR (%) | 874.30 | 753.32 | 478.43 | 190.52 |
| lowest T/C (%) | | | | |
| 11th day | 13.33 | 9.76 | 20.64 | 9.81 |
| 15th day | 10.52 | 6.75 | 8.47 | 2.36 |

In the experimental test using the model of nude mice with cancer, by administering the compound 1 together with cisplatin, the effect of inhibiting tumor growth in the cisplatin resistant cancer cell line (PC-14/CDDP) was exhibited. This proves that the compound 1 has the effect of reducing the resistance of and increasing the sensitivity of cancer cells to cisplatin.

As apparent from above examples, the compound represented by the general formula [1] according to the present invention has not only the effect of overcoming the resistance to various anticancer drugs, but also the effect of enhancing the effect of various anticancer drugs on anticancer-drug sensitive cells. Thus, this compound has excellent effects not only on resistant cells but also on sensitive cells, and is expected to provide an extremely effective drug, particularly for treating a cancer having an acquired resistance to an anticancer drug. Thus, the pharmaceutical composition of the present invention, which contains the compound represented by the general formula [1] and an anticancer drug, is effective to the treatment of cancers, particularly to the treatment of a cancer having an acquired resistance to an anticancer drug. Further, the pharmaceutical kit of the present invention is suitable for administration of a drug for overcoming a resistance to an anticancer drug or a drug for enhancing an effect of an anticancer drug together with the anticancer drug, and is in particular effective to the treatment of a cancer having the acquired resistance to the anticancer drug. According to the method for treating cancer of the present invention, by administering the compound represented by the general formula [1] together with an anticancer drug, an excellent carcinostatic effect is exhibited even to a cancer having the acquire resistance to the cancer drug.

The present application is based on Japanese Patent Application No. Hei 11-139196 filed in Japan in 1999, and the entire disclosure thereof is incorporated hereinto.

What is claimed is:

1. A method for overcoming resistance to an anticancer drug selected from the group consisting of platinum complex, adriamycin and taxol comprising administering to a patient in need thereof said anticancer drug and a compound, 4-[3-(4-benzylpiperidine-1-yl)propionyl]-7-methoxy-2,3,4,5-tetrahydro-1,4benzothiazepine.

2. A method for enhancing an effect of an anticancer drug selected from the group consisting of cisplatin, carboplatin, nedaplatin, adriamycin and taxol comprising administering to a patient in need thereof said anticancer drug and a compound, 4-[3-(4-benzylpiperidine-1-yl)propionyl]-7-methoxy-2,3,4,5-tetrahydro-1,4benzothiazepine.

3. A method for reducing resistance of cancer to an anticancer drug selected from the group consisting of cisplatin, carboplatin, nedaplatin, adriamycin and taxol comprising administering to a patient in need thereof said anticancer drug and a compound, 4-[3-(4-benzylpiperidine-1-yl)propionyl]-7-methoxy-2,3,4,5-tetrahydro-1,4-benzothiazepine.

4. A method for increasing a sensitivity of cancer to an anticancer drug selected from the group consisting of cisplatin, carboplatin, nedaplatin, adriamycin and taxol comprising administering to a patient in need thereof said anticancer drug and a compound, 4-[3-(4-benzylpiperidine-1-yl)propionyl]-7-methoxy-2,3,4,5-tetrahydro-1,4-benzothiazepine.

5. A method for treating a lung cancer or leukemia which overcomes resistance to an anticancer drug selected from the group consisting of cisplatin, carboplatin, nedaplatin, adriamycin and taxol, which comprises administering to a patient in need thereof an anticancer drug selected from the group consisting of cisplatin, carboplatin, nedaplatin, adriamycin and taxol and a compound 4-[3-(4-benzylpiperidine-1-yl)propionyl]-7-methoxy-2,3,4,5-tetrahydro-1,4benzothiazepine.

6. A method for treating lung cancer or leukemia comprising administering to a patient in need thereof an anticancer drug selected from the group consisting of platinum complex, adriamycin and taxol and a compound 4-[3-(4-benzylpiperidine-1-yl)propionyl]-7-methoxy-2,3,4,5-tetrahydro-1,4-benzothiazepine.

* * * * *